United States Patent
Nita

Patent Number: 5,693,033
Date of Patent: Dec. 2, 1997

[54] BARIUM FEEDING DEVICE FOR X RAY GI STUDIES

[76] Inventor: Octavian Nita, 6913 W. Clinton Ave., Cleveland, Ohio 44102

[21] Appl. No.: 612,295

[22] Filed: Mar. 7, 1996

[51] Int. Cl.$^6$ .................................................. A61M 5/00
[52] U.S. Cl. .......................... 604/264; 215/11.3; 220/709
[58] Field of Search ................................ 239/16, 24, 33, 239/502; 215/11.1, 11.3; 220/666, 705, 707–710, 720; 604/77, 78, 79, 280, 264; 606/234, 236; 222/158, 527, 529, 564

[56] References Cited

U.S. PATENT DOCUMENTS

| | | | |
|---|---|---|---|
| 3,645,262 | 2/1972 | Harrigan | 128/222 |
| 4,301,934 | 11/1981 | Forestal | 215/11 D |
| 4,813,556 | 3/1989 | Lawrence | 215/11.3 |
| 4,994,076 | 2/1991 | Guss | 606/236 |
| 5,509,551 | 4/1996 | Terrell, II | 215/229 |

*Primary Examiner*—Corrine M. McDermott
*Assistant Examiner*—Deborah Blyveis

[57] ABSTRACT

A thin, long tube (1) made of transparent semi-rigid plastic having a closed end (2) and an open, enlarged and threaded end (3) for feeding attachments: baby nipple (6) or feeding straw (7). Semi-rigid plastic signify that the tube can be squeezed (compressed) between the fingers of the operator in order to force the liquid of the tube. The tube has volume measuring marks (8) starting at the closed end and a self locking accordion-like portion (4) close to the open end. The tube contains a wave breaking insert (5) made of coiled (helicoidal) or brush-like plastic.

1 Claim, 4 Drawing Sheets

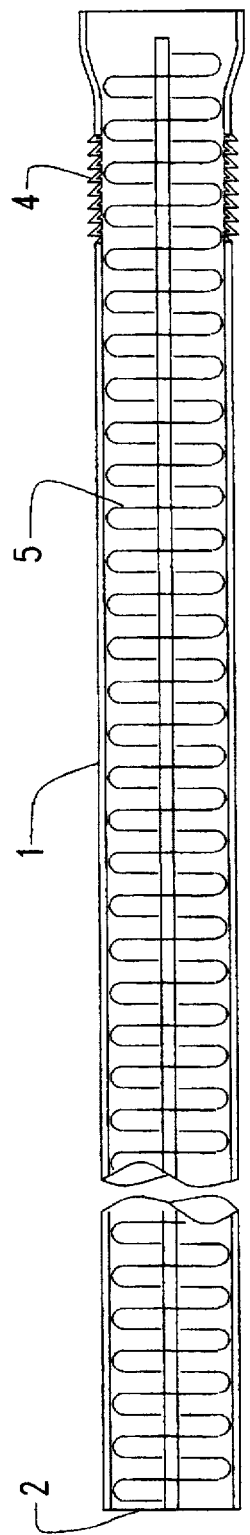
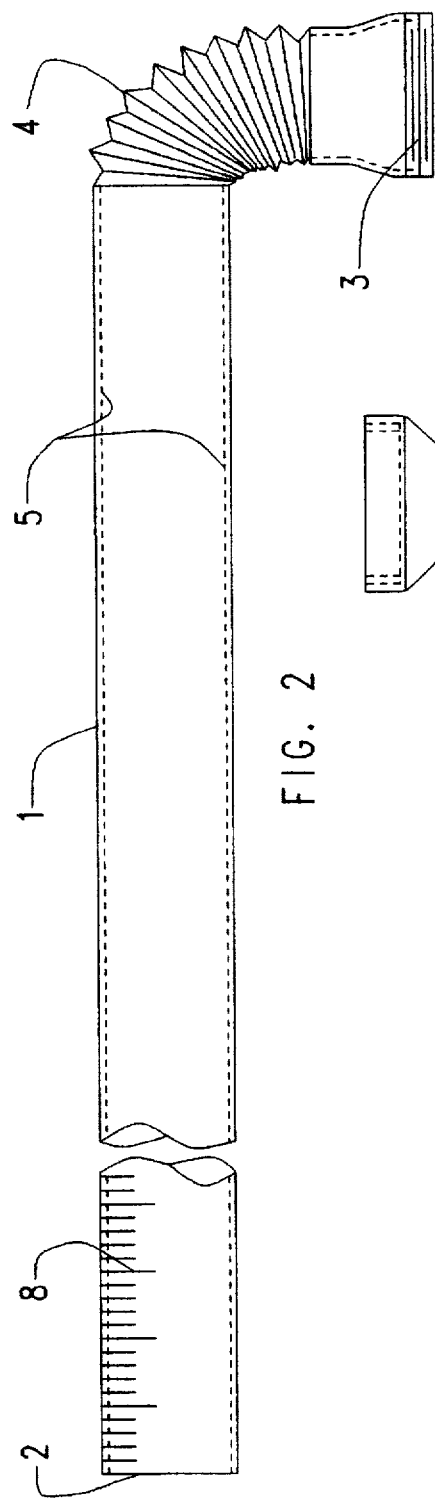
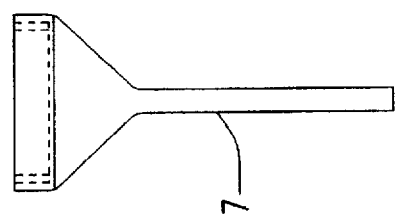
FIG. 1
FIG. 2
FIG. 3
FIG. 4

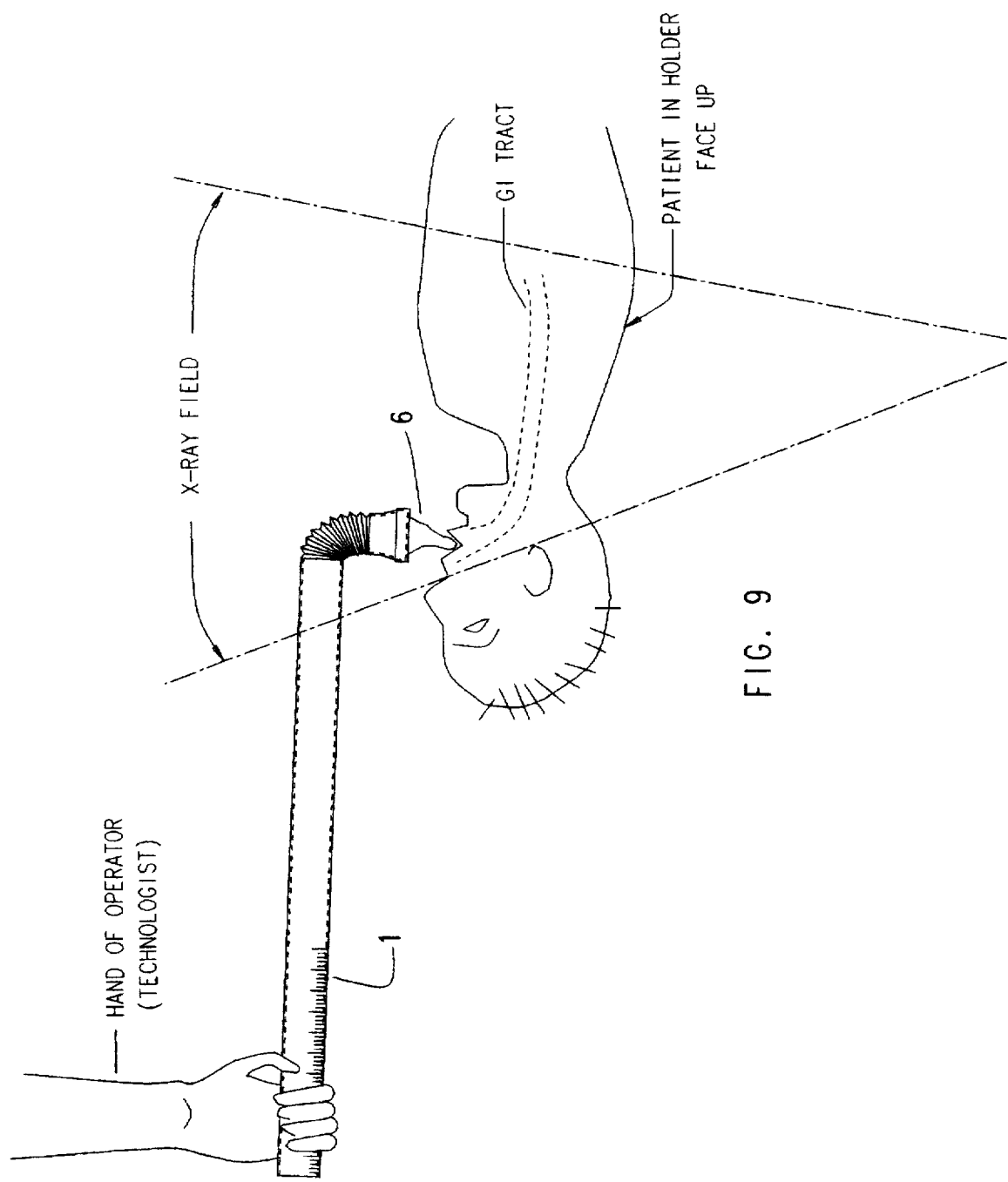

BARIUM FEEDING DEVICE FOR X RAY GI STUDIES

FIELD OF THE INVENTION

The present invention relates to a device for feeding barium, or other oral contrast media, to patients unable to feed themselves (infants and critically ill adults), under X Ray fluoroscopic examination of the Gastro-Intestinal (GI) tract.

BACKGROUND-DISCUSSION OF THE PRIOR ART

Currently, these patients are fed by a person (usually a technologist) holding a bottle or a container with a straw. The person feeding will wear a heavy lead glove which often interferes with the area being imaged, makes difficult holding the bottle, and most damaging, exposing that person to an important amount of radiation to the hand, arm, chest, neck and head. Not only that the hand (even protected by a lead glove) is very close to the central ray, but because of the position of the fluoroscopy tower, the person feeding has to bend down close to the patient, thus, the upper body of the person feeding receives plenty of scattered radiation from the patient and the fluoro machine itself.

At the present time, there is no known device specifically designed to accomplish the task of feeding contrast media to the patient.

OBJECTS AND ADVANTAGES

It is well known that the greater protection from radiation is the distance.

The proposed device will make possible feeding from a protective distance and allows for a high maneuverability. The person feeding will be far away from the X Ray field and the lead glove will not interfere with the imaging of the body part.

Further objects and advantages of my invention will become apparent from a consideration of the drawings and ensuing description.

DESCRIPTION OF INVENTION

The device consists of a transparent plastic tube (1) closed at one end (2) and threaded (3) at the other. The threaded end (3) can be bent at a desired angle due to an accordion like portion (4), self locking (similar to the drinking straws). Inside the tube (1) there is a wave breaking device (5) consisting of a coiled piece of plastic, brush-like plastic, or any other elastic structure easy to obtain and insert in the tube (1). This wave breaking insert (5) will stop the fluid from rushing towards an end when tilting the tube (1), though allowing the tube (1) to be squeezed in order to push some fluid out at the open end (3). The open end (3) is enlarged and threaded, forming a funnel through which the tube (1) can be filled with fluid (barium or other liquid contrast media). The thread can fit either a standard baby nipple (6) or a short thin tube (7), straw-like, for adults.

The tube (1) will have marks (8), starting at the closed end (2), to show the quantity of the remaining liquid.

The device is of a single use, disposable type and is supposed to be sterilized before use.

OPERATION OF INVENTION

The method of feeding (FIGS. 8 & 9) is comfortable and will accommodate any position desirable for the patient: LPO, AP, LATERAL, are easy to obtain. The person feeding will hold the tube with the arm extended, will adjust the angle of the bellows and will insert the feeding tip in the mouth of the patient. The weight of the barium is uniformly distributed along the length of the tube so is not stressful for the wrist of the feeder.

Usually the pediatric patients will provide the necessary suction to extract the barium from the nipple, and if not so, a little squeeze of the tube will provide a quantity of the barium in the mouth and stimulate the swallowing process.

Critically ill adults cannot regularly provide enough suction in order to drink through a straw. It is customary in X Ray GI departments to feed them barium using a syringe and an extension tubing into their mouth. This method will allow enough distance for the operator to be safe but the extension tubing has to be repositioned constantly and most likely, held by hand in the mouth of the patient.

By using the present device with the adult straw-like soft attachment, the tip can be inserted from a distance into the mouth of the patient and the required amount of barium squeezed will be delivered for the study.

Attached is a drawing of the device. Dimensions may vary according to the area of use (infants or adults), optimum being around 2 to 3 cm. diameter and 50 to 60 cm. in length.

DESCRIPTION OF DRAWINGS

FIG. 1 is a cross-sectional view of the Barium Feeding Device containing all the elements recited in Specification. The Device is not shown its actual size, interruption marks are present.

FIG. 2 is a view of the invention with the self-locking portion bent at 90 degrees.

FIG. 3 is a view of one of the attachments, a standard baby nipple.

FIG. 4 is a view of the feeding straw attachment.

FIG. 8 and FIG. 9 show the Operation of Invention. Note that the hand (and the body) of the technologist is outside the X Ray Field, while still having control of the feeding regardless of the position in which the restrained patient is placed. The barium reaches the mouth of the patient either by gravity or by the pressure generated by the hand of technologist squeezing the semi-rigid tube.

Figure 5:
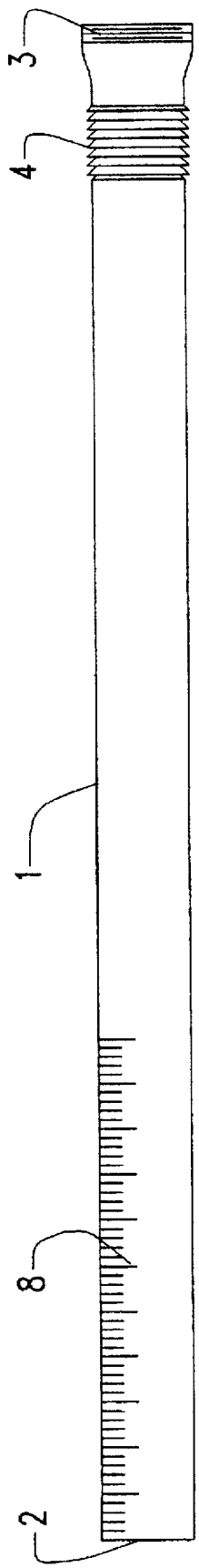
FIG. 5 is a view of the semi-rigid tube without the wave breaking device insert.
Figure 6:
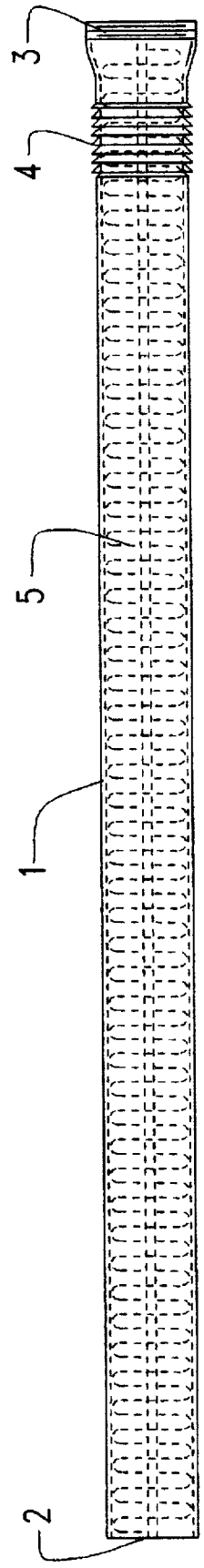
FIG. 6 is a view of the tube with the wave breaking device inserted inside and extending the whole length. The tube is shown reduced in size, actual dimensions being 2 to 3 cm. diameter and 50 to 60 cm in length, as stated in Specification.
Figure 7:
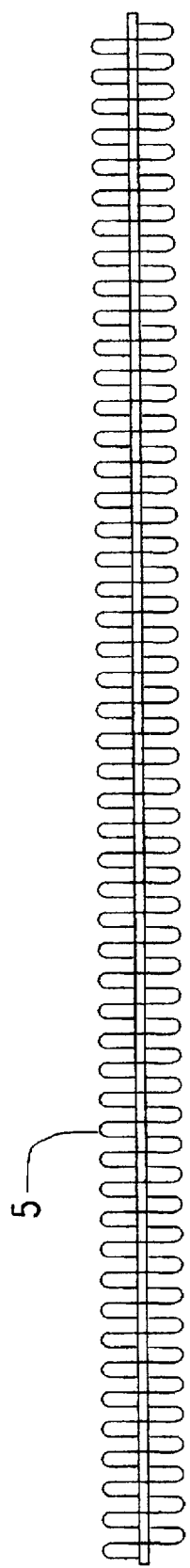
FIG. 7 is a view of the wave breaking insert consisting of coiled (helicoidal) or brush-like plastic, as described in Specification.
Figure 8:
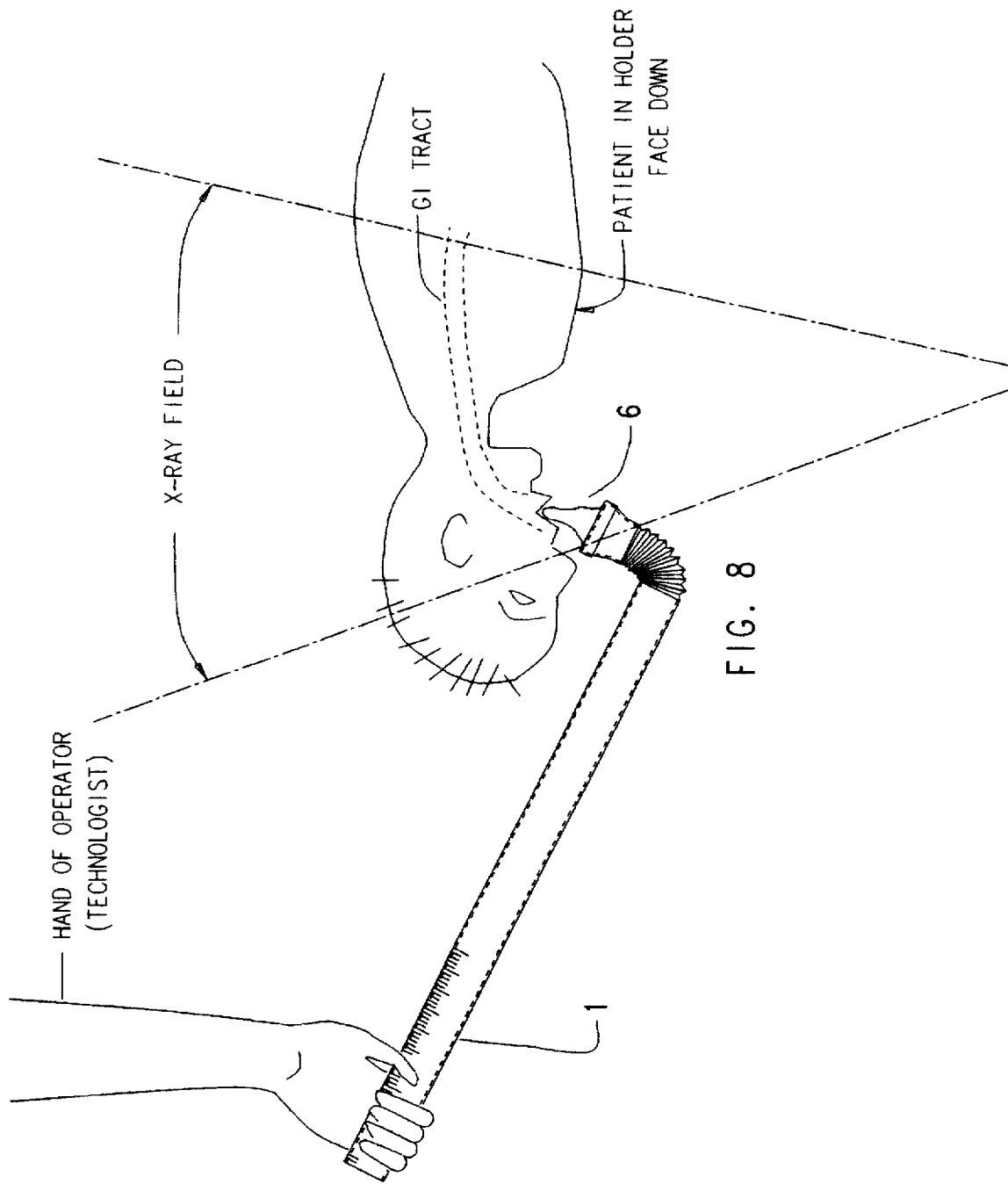

I claim:

1. A barium feeding device for X Ray GI studies comprising:

(a) a transparent semi-rigid tube made of plastic material with a closed end and an enlarged threaded open end with a self locking accordion-like portion close to the open end;

(b) said tube containing a wave breaking insert made of coiled or brush-like plastic;

(c) said tube having marks for the quantity of liquid beginning at the closed end;

(d) a feeding straw attachment comprising a straw-like end and a threaded end that attaches to the open end of the tube.

* * * * *